(12) United States Patent
Hayden

(10) Patent No.: US 7,026,120 B2
(45) Date of Patent: Apr. 11, 2006

(54) PROBES FOR DETECTING TUMOR CELLS

(75) Inventor: Mark A. Hayden, Ingleside, IL (US)

(73) Assignee: Abbott Laboratories, Abbott Park, IL (US)

( * ) Notice: Subject to any disclaimer, the term of this patent is extended or adjusted under 35 U.S.C. 154(b) by 297 days.

(21) Appl. No.: 10/122,568

(22) Filed: Apr. 15, 2002

(65) Prior Publication Data

US 2003/0219746 A1 Nov. 27, 2003

(51) Int. Cl.
*C12Q 1/68* (2006.01)
*C12P 19/34* (2006.01)
*C07H 21/04* (2006.01)

(52) U.S. Cl. .................. 435/6; 435/91.1; 435/91.2; 536/23.1; 536/24.3

(58) Field of Classification Search .............. 435/6, 435/91.1, 91.2; 536/23.1, 24.3
See application file for complete search history.

(56) References Cited

U.S. PATENT DOCUMENTS 5,474,796 A * 12/1995 Brennan ............... 427/2.13
5,766,888 A 6/1998 Sobel et al.
6,203,992 B1 * 3/2001 Granados et al. ............. 435/6

OTHER PUBLICATIONS

Tyagi et al; Nature Biotechnology, vol. 16, pp. 49-53, Jan. 1998.*
Rudd et al; International Journal of Cancer, vol. 80, pp. 119-125; 1999.*
Van Trappen et al; The Lancet, Jan. 6, 2001; vol. 357, pp. 15-20.*
Trummer et al, Journal of hematotherapy and stem cell research; vol. 9, pp. 275-284, Apr. 2000.*
Buck et al; Biotechniques; 1999, 27(3):528-536.*
Genbank Accession No. A83616, Jan. 2000.*
Datta, Y.H. et al., "Sensitive Detection of Occult Breast Cancer by the Reverse-Transcriptase Polymerase Chain Reaction", Journal of Clinical Oncology, vol. 13 (No. 3), p. 475-482 (1994).
"Immunobead RT-PCR: A Sensitive Method for Detection of Circulating Tumor Cells", BioTechniques, vol. 21, p. 100-105 (1997).
Ruud et al., "Identification of a Novel Cytokeratin 19 Pseudogene that may interfere with Reverse Transcriptase-Polymerase Chain reaction Assays Used to Detect Micrometastatic Tumor Cells", International Journal of Cancer: 80, 119-125 (Jan. 1999).
Stasiak et al., "Sequence of cDNA coding for Human Keratin 19",Nucleic Acids Reasearch. vol. 15, p. 10058 (1987).

* cited by examiner

*Primary Examiner*—Jehanne Sitton

(57) ABSTRACT

Probes are provided that are useful for detecting CK19 target sequence in a test sample.

5 Claims, No Drawings

PROBES FOR DETECTING TUMOR CELLS

FIELD OF THE INVENTION

The present invention relates to oncology and, in particular, it relates to oligonucleotides for detecting carcinoma in a test sample.

BACKGROUND OF THE INVENTION

Studies have suggested that the presence of epithelial cells in the hematopoietic system indicates the spread of cancer from a localized area to other parts of the body (also known as metastisis). This discovery is important since metastisis is diagnostic of certain stages of cancer, and decisions concerning the proper treatment of a cancer patient are largely dependent upon properly characterizing the stage of the disease. In particular, treatments for patients having localized cancer can be vastly different from treatments given to patients in metastatic stages of cancer.

With the advent of nucleic acid amplification reactions such as the polymerase chain reaction (PCR), epithelial cells present in the hematopoietic system can be detected at the nucleic acid level instead of at the protein level. Hence, problems associated with crossreactive antibodies are avoided. Additionally, it is well known that nucleic acid amplification reactions are significantly more sensitive than more conventional antibody based assay methods. Amplification based assays for detecting epithelial cells in the blood stream have therefore provided significant advantages over immunocytological assay methods for detecting early stages of metastatic cancer.

PCR based assays employed to detect epithelial cells in the hematopoletic system have been reported in the literature. Most of these assays target a nucleic acid sequence encoding cytokeratin 19 (CK19), a protein found on the surface of epithelial cells. However, many psuedogenes (comprising a nucleic acid sequence that closely mimics the gene for CK19) are present in the human genome. Thus, one challenge facing those developing amplification assays to detect a CK19 target sequence is to design assays that amplify and detect a sequence from the CK19 gene but not the closely related pseudogene.

Additionally, it is well known that amplification primer sequences can be selected based upon computer comparisons of closely related sequences. Theoretically, sequences selected in this manner effectively should produce copies of the selected target sequence when employed according to nucleic acid amplification principles. Notwithstanding, the theoretical efficacy of sequences selected in the above manner, it is often times true that such sequences do not produce acceptable amounts of amplification product. Unfortunately, this phenomenon is not understood. Accordingly, while primers initially can be screened using computer programs efficacy cannot be adequately determined until such primers are employed in practice.

A further challenge faces those designing PCR assays that use microparticle capture based detection procedures for detecting amplification products. Specifically, amplified target sequences detected with the assistance of microparticles must be sufficiently short so that amplification product captured on the microparticle does not interfere with the capture of additional amplification product. Accordingly, those choosing to detect amplification products with the assistance of a microparticle are faced with an added restriction in terms of selection of a suitable target sequence. In particular, suitable target sequences are constrained to sequences that are relatively short.

U.S. Pat. No. 6,203,992 discloses a PCR based method for detecting CK 19 target sequence. Unfortunately, the method disclosed by the '992 patent does not have a desirable ability to accurately quantify the level of CK 19 present in a sample.

There is therefore a need in the art for an improved method and sequences that can be employed according to nucleic acid amplification principles to detect a CK 19 target sequence that provide a greater degree of quantitation.

SUMMARY OF THE INVENTION

The present invention provides nucleic acid sequences that can be used to specifically and sensitively detect the expression of cytokeratin 19 (CK 19). In particular, primers sequences employed in the present invention are designated SEQ ID NO 2 and SEQ ID NO 3. Probes comprising sequences identified herein by SEQ ID NO 4 can be used to usefully quantify the level of CK 19 in a sample. Combinations of the above sequences can be provided in kits along with other reagents for performing an amplification reaction to detect CK 19 in peripheral blood and therefore circulating cancer cells or cancer in the metastatic stages of the disease.

The CK 19 target sequence, designated herein as SEQ. ID. NO. 1, can be amplified by forming a reaction mixture comprising nucleic acid amplification reagents, a test sample containing a CK 19 target sequence. Any suitable means of amplifying CK 19 can be used. Preferably, the amplified sequence is less than 200 nucleotides in length. Preferably, the CK 19 target is amplified using PCR employing a primer set containing SEQ ID NOs. 2 and 3 is used.

Following amplification, the amplified target sequence can be detected. For example, any probe or any combination of the probes that contains the sequence designated SEQ ID NO. 4 can be employed to hybridize to the amplified target sequence to form a probe/product hybrid. The probe/product hybrid can then be detected using any suitable technique, including without limitation microparticle capture techniques. The primers or probes optionally can be labeled to capture and detect the amplified target sequence and therefore indicate the presence of the target sequence in the test sample.

DETAILED DESCRIPTION OF THE INVENTION

The present invention provides reagents, methods, and kits for amplifying and detecting a CK-19 target sequence in a test sample. In particular, 5' CCGCGACTAC AGCCACTACT ACAC 3'[SEQ ID NO: 2] and 5' GAGCCTGTTC CGTCTCAAA 3' [SEQ ID NO: 3] can be employed as amplification primers to amplify the CK 19 target sequence which is GGCCTGGGCC CTCCCGCGAC TACAGCCACT ACTACACGAC CATCCAGGAC CTGCGGGACA AGATTCTTGG TGCCACCATT GAGAACTCCA GGATTGTCCT GCAGATCGAC AACGCCCGTC TGGCTGCAGA TGACTTCCGA ACCAAGTTTG AGACGGAACA GGCTCTGCGC ATGAGCGTGG [SEQ ID NO: 1]. However, other suitable methods of amplifying the DNA, which are known in the art, such as rolling circle amplification, TMA, NASBA, ligase chain reaction, and the like can also be used It was discovered that these primers specifically and sensitively produce an amplification product that is amenable to microparticle capture and detection techniques.

The amplified DNA is detected using a probe having at least 15, more preferably at least 20, and yet more preferably all 24, of the following 21 nucleotides: 5' GTGCCACCAT TGAGAACTCC AGGA 3' [SEQ ID NO: 4], such that specific detection of CK 19 is achieved in a test sample comprising amplified CK 19 DNA.

More preferably, the amplified DNA is detected using a probe having at least 15, more preferably 24, and yet more preferably all 29 nucleotides of the sequence 5' TGGTGC-CACC ATTGAGAACT CCAGGATTG 3' [SEQ ID NO: 5]. In a more preferred embodiment, the probe is a molecular beacon probe containing a flourescer and a moiety that detectably changes the emission of the fluorescer when the molecular beacon probe is bound to the amplified target CK 19, compared to when the molecular beacon probe is not bound to the target.

In a yet more preferred embodiment, the probe is a molecular beacon probe having the sequence 5' CGTGGT-GCCA CCATTGAGAA CTCCAGGACC ACG 3' [SEQ ID NO: 6]. For clarity, this sequence can be represented as: CGTGGT-GCCACCATTGAGAACTCCAGG-ACCACG [SEQ ID NO: 6] wherein the bolded sequence is capable of hybridizing with the CK 19 target sequence, and the two sequences at either end of the oligonucleotide are complementary to each other.

In an equally preferred embodiment, the probe is a molecular beacon having the sequence 5' CCGTGCCACC ATTGAGAACT CCAGGATTGC ACGG 3' [SEQ ID NO: 7]. For clarity, this sequence can be represented as: CCGTGC-CACCATTGAGAACTCCAGGATT-GCACGG [SEQ ID NO: 7] wherein the bolded sequence is capable of hybridizing with the CK 19 target sequence, and the two sequences at either end of the oligonucleotide are complementary to each other.

Alternatively, the present invention also provides oligonucleotides that are complementary to any of the oligonucleotides described above, other than SEQ ID NOS: 1–3. It will be appreciated that any suitable modification or derivatization of these oligonucleotides can also be used in the context of the present invention, so long as the specificity of the oligonucleotide for the CK 19 target is not substantially diminished.

In one particular embodiment, the probe is a molecular beacon probe comprising fluorescein and a quencher. Any suitable quencher including without limitation Dabcyl, Dabsyl, Dark Hole Quencher, and the like can be used.

The probe is preferably less than 140 nucleotides in length, more preferably less than 70 nucleotides in length, more preferably less than 50 nucleotides in length, and yet more preferably less than 35 nucleotides in length.

The probe sequences of the present invention can be employed to insure specificity and detect the amplification product.

Particularly when the probe is a molecular beacon, it preferably is used in an assay with primers such that the ratio of signal to noise is greater than about 3, more preferably is greater than about 4, and yet more preferably is greater than about 5. In the context of the present invention, the signal generated directly or indirectly by the probe in the presence of the target sequence divided by the signal generated directly or indirectly by the probe in the presence of a polyA nucleotide. When the probe is a molecular beacon probe, therefore, the term "signal to noise" means the raw fluorescence signal of the beacon in the presence of amplicon divided by the raw fluorescence signal of the same beacon in the negative control (poly A only). Moreover, the signal to noise ratio is measured after a suitable number of cycles under ordinary condition with a quantity of target that is significantly greater than the minimum detectable quantity, but which is not so great as to quench the generated signal (i.e., induce a "hook" effect). In the Example below, the signal was measured during the last cycle of a 45-cycle thermocycling reaction. For clarity, correction or subtraction for background signal is not part included in the calculation of signal to noise.

The primer and probe sequences disclosed herein, may comprise deoxyribonucleic acid (DNA), ribonucleic acid (RNA) or nucleic acid analogs such as uncharged nucleic acid analogs including but not limited to peptide nucleic acids (PNAs) which are disclosed in International Patent Application WO 92/20702 or morpholino analogs which are described in U.S. Pat. Nos. 5,185,444, 5,034,506, and 5,142,047. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, the sequences can be labeled using methodologies well known in the art such as described in U.S. patent applications Nos. 5,464,746; 5,424,414; and 4,948,882. It will be understood, however, that the sequences employed as primers should at least comprise DNA at the 3' end of the sequence and preferably are completely comprised of DNA.

A "target sequence" as used herein means a nucleic acid sequence that is detected, amplified, both amplified and detected or otherwise is complementary to one of the sequences herein provided. While the term target sequence is sometimes referred to as single stranded, those skilled in the art will recognize that the target sequence may actually be double stranded.

The term "test sample" as used herein, means anything suspected of containing the target sequence. The test sample can be derived from any biological source, such as for example, blood, bronchial alveolar lavage, saliva, throat swabs, ocular lens fluid, cerebral spinal fluid, sweat, sputa, urine, milk, ascites fluid, mucous, synovial fluid, peritoneal fluid, amniotic fluid, tissues such as heart tissue and the like, or fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma from blood, disrupting cells, preparing liquids from solid materials, diluting viscous fluids, filtering liquids, distilling liquids, concentrating liquids, inactivating interfering components, adding reagents, purifying nucleic acids, and the like. Most typically, the test sample will be peripheral blood.

SEQ ID NOs: 2 and 3 can be used as amplification primers according to amplification procedures well known in the art to amplify the target sequence. Preferably, the sequences provided herein are employed according to the principles of the polymerase chain reaction (PCR) described in U.S. Pat. Nos. 4,683,195 and 4,683,202. It will be understood by those skilled in the art that in the event that the target sequence is RNA, a reverse transcription step should be included in the amplification of the target sequence. Enzymes having reverse transcriptase activity, such as Taq polymerase, are well known for activity capable of synthesizing a DNA sequence from an RNA template. Reverse transcription PCR (RT PCR) is well known in the art and described in U.S. Pat. Nos. 5,310,652 and 5,322,770.

Thus, amplification methods of the present invention generally comprise the steps of (a) forming a reaction mixture comprising nucleic acid amplification reagents, at least one amplification primer (i.e. SEQ. ID.NO. 2 or 3), and a test sample suspected of containing a target sequence; and (b) subjecting the mixture to amplification conditions to generate at least one copy of a nucleic acid sequence complementary to the target sequence. It will be understood that step (b) of the above method can be repeated several times by thermal cycling the reaction mixture as is well known in the art.

As stated above, the reaction mixture comprises "nucleic acid amplification reagents" that include reagents which are well known and may include, but are not limited to, an enzyme having polymerase activity (and, as necessary, reverse transcriptase activity), enzyme cofactors such as magnesium or manganese; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

"Amplification conditions" are defined generally as conditions which promote hybridizing or annealing of primer sequences to a target sequence and subsequent extension of the primer sequences. It is well known in the art that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures which are close to (i.e. within 10° C.) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the Tm of the primers or probe. Thus, obtaining suitable hybridization conditions for a particular primer, probe, or primer and probe set is well within ordinary skill of one practicing this art.

The amplification product produced as above can be detected during or subsequently to the amplification of the CK-19 target sequence using any suitable method and the probe of the present invention. Thus, amplified CK-19 target sequence can be detected by a method including the steps of (a) hybridizing at least one hybridization probe of the present invention to the nucleic acid sequence complementary to the target sequence, so as to form a hybrid comprising the probe and the nucleic acid sequence complementary to the target sequence; and (b) detecting the hybrid as an indication of the presence of the presence of the target sequence in the test sample.

Hybrids formed as above can be detected using labels that can be used to separate or detect or separate and detect such hybrids.

The oligonucleotides of the present invention can include a molecule or moiety having a property or characteristic which is capable of detection (a "label"). A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

According to another embodiment, a combination of specific binding members and directly detectable labels can be employed to detect hybrids. For example, specific binding members can be introduced in the hybrids using primers labeled with specific binding members. A directly detectable label can be incorporated into the hybrids using a probe that has been labeled with a directly detectable label. Hence, hybrids can be immobilized to a microparticle using the specific binding member and directly detected by virtue of the label on the probe. It will be understood that other detection configurations are a matter of choice for those skilled in the art.

According to the one preferred embodiment where the probe initially is part of the amplification mixture, it is preferable to select primers, probes and amplification conditions such that the probe sequence has a lower melt temperature than the primer sequences so that upon placing the reaction mixture under amplification conditions copies of the target sequence or its complement are produced at temperature above the Tm of the probe. After such copies are synthesized, they are denatured and the mixture is cooled to enable the formation of hybrids between the probes and any copies of the target or its complement. The rate of temperature reduction from the denaturation temperature down to a temperature at which the probes will bind to single stranded copies is preferably quite rapid (for example 8 to 15 minutes) and particularly through the temperature range in which an enzyme having polymerase activity is active for primer extension. Such a rapid cooling favors copy sequence/probe hybridization rather that primer/copy sequence hybridization and extension.

The following examples are provided to further illustrate the present invention and but should not be construed to limit the scope of the invention.

EXAMPLE

The following example demonstrates detection of cytokeratin 19 (CK19) using the present inventive probe. More specifically, this example demonstrates that a molecular beacon probe of the present invention performs well in a PCR assay capable of detecting and quantifying the amount of CK 19 target sequence present in a sample. Furthermore, the present example demonstrates that the molecular beacon probe of the present invention is surprisingly superior to another molecular beacon that is of similar size and design as the molecular beacon of the present invention.

In the following examples, SEQUENCE ID NO. 2, and SEQUENCE ID NO. 3 are used as amplification primers specific for the CK19 target sequence. Each molecular beacon was labeled at the 5' end with fluorescein and at the 3' end with a suitable fluorescence quencher (dabcyl for SEQ ID NOS: 6 and 7, and Black Hole Quencher (BHQ) for SEQ ID NO: 8), such that the molecular beacon emits a detectably stronger signal when bound to the target sequence.

PCR was performed on a test sample containing variable amounts of CK 19 RNA as follows. Reverse transcription reagents were added to the sample, which was then incubated at 48° C. for 45 min to reverse transcribe CK 19 RNA. This was followed by a 2 minute incubation at 94° C. to inactivate the reverse transcriptase. Then, in the presence of amplification reagents, the reaction was cycled 45 times at 94° C. for 15 seconds, 58° C. for 20 seconds. Following amplification, the reaction was incubated at 68° C. for 20 seconds, and then at 35° C. for 30 seconds during which time the fluorescence of the beacon was determined.

The signal to noise ratio (S/N) was calculated for a molecular beacon of the present invention, CGTGGTGCCA CCATTGAGAA CTCCAGGACC ACG [SEQ ID NO: 6] and for a comparison molecular beacon, CGTGCGGACCT-GCGGGACAAGATGCACG [SEQ ID NO: 8]. The signal to noise ratio of the beacon having SEQ ID NO: 6 was 5.2, whereas the signal to noise ration of the beacon having a SEQ ID NO: 8 was 2.6.

In a similar experiment the beacon having SEQ ID NO; 7 was similar to that of the beacon having SEQ ID NO: 7.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

---

What is claimed is:

1. A composition of matter for detecting a CK19 target sequence comprising a nucleic acid selected from the group consisting of SEQ ID NO: 6, SEQ ID NO: 7, the complements of SEQ ID NO: 6, and the complement of SEQ ID NO: 7.

2. The composition of matter of claim 1, wherein the nucleic acid is selected from the group consisting of SEQ ID NO: 6 and SEQ ID NO: 7.

3. The composition of matter of claim 2, further comprising a fluorescent label and a fluorescence quencher.

4. A method of amplifying a CK19 target sequence comprising the steps of:

(a) forming a reaction mixture comprising nucleic acid amplification reagents, the composition of matter of claim 1, and a test sample suspected of containing a target sequence; and (b) subjecting the mixture to amplification conditions to generate at least one copy of a nucleic acid sequence complementary to the target sequence.

5. A kit for amplifying a CK19 target sequence comprising:

(a) the composition of matter of claim 1; and
(b) amplification reagents.

* * * * *

SEQUENCE LISTING

```
<160> NUMBER OF SEQ ID NOS: 8

<210> SEQ ID NO 1
<211> LENGTH: 180
<212> TYPE: DNA
<213> ORGANISM: Homo sapiens

<400> SEQUENCE: 1
ggcctgggcc ctcccgcgac tacagccact actacacgac catccaggac ctgcgggaca      60
agattcttgg tgccaccatt gagaactcca ggattgtcct gcagatcgac aacgcccgtc     120
tggctgcaga tgacttccga accaagtttg agacggaaca ggctctgcgc atgagcgtgg     180

<210> SEQ ID NO 2
<211> LENGTH: 24
<212> TYPE: DNA
<213> ORGANISM: Artificial Sequence
<220> FEATURE:
<223> OTHER INFORMATION: Amplification Primer

<400> SEQUENCE: 2
ccgcgactac agccactact acac                                              24

<210> SEQ ID NO 3
<211> LENGTH: 19
<212> TYPE: DNA
<213> ORGANISM: Artificial Sequence
<220> FEATURE:
<223> OTHER INFORMATION: Amplification Primer

<400> SEQUENCE: 3
gagcctgttc cgtctcaaa                                                    19

<210> SEQ ID NO 4
<211> LENGTH: 24
```

```
-continued

<212> TYPE: DNA
<213> ORGANISM: Artificial Sequence
<220> FEATURE:
<223> OTHER INFORMATION: Probe

<400> SEQUENCE: 4
gtgccaccat tgagaactcc agga                                              24

<210> SEQ ID NO 5
<211> LENGTH: 29
<212> TYPE: DNA
<213> ORGANISM: Artificial Sequence
<220> FEATURE:
<223> OTHER INFORMATION: Probe

<400> SEQUENCE: 5
tggtgccacc attgagaact ccaggattg                                         29

<210> SEQ ID NO 6
<211> LENGTH: 33
<212> TYPE: DNA
<213> ORGANISM: Artificial Sequence
<220> FEATURE:
<223> OTHER INFORMATION: Molecular Beacon Probe

<400> SEQUENCE: 6
cgtggtgcca ccattgagaa ctccaggacc acg                                    33

<210> SEQ ID NO 7
<211> LENGTH: 34
<212> TYPE: DNA
<213> ORGANISM: Artificial Sequence
<220> FEATURE:
<223> OTHER INFORMATION: Molecular Beacon Probe

<400> SEQUENCE: 7
ccgtgccacc attgagaact ccaggattgc acgg                                   34

<210> SEQ ID NO 8
<211> LENGTH: 28
<212> TYPE: DNA
<213> ORGANISM: Artificial Sequence
<220> FEATURE:
<223> OTHER INFORMATION: Molecular Beacon Probe

<400> SEQUENCE: 8
cgtgcggacc tgcgggacaa gatgcacg                                          28
```